(12) United States Patent
De Volpi

(10) Patent No.: US 8,946,645 B2
(45) Date of Patent: Feb. 3, 2015

(54) RADIATION-MONITORING DIAGNOSTIC HODOSCOPE SYSTEM FOR NUCLEAR-POWER REACTORS

(71) Applicant: Alexander De Volpi, Oceanside, CA (US)

(72) Inventor: Alexander De Volpi, Oceanside, CA (US)

(*) Notice: Subject to any disclaimer, the term of this patent is extended or adjusted under 35 U.S.C. 154(b) by 0 days.

(21) Appl. No.: 13/815,070

(22) Filed: Jan. 28, 2013

(65) Prior Publication Data
US 2014/0209808 A1 Jul. 31, 2014

(51) Int. Cl.
*G01T 1/24* (2006.01)
*G01T 3/06* (2006.01)
*G21C 17/00* (2006.01)

(52) U.S. Cl.
CPC .. *G01T 3/06* (2013.01); *G21C 17/00* (2013.01)

USPC .................................................. 250/370.09

(58) Field of Classification Search
USPC ........................................ 250/370.08, 370.09
See application file for complete search history.

(56) References Cited

U.S. PATENT DOCUMENTS

| | | | | |
|---|---|---|---|---|
| 4,870,669 | A * | 9/1989 | Anghaie et al. | 378/87 |
| 5,345,479 | A * | 9/1994 | Graham | 376/250 |
| 5,774,515 | A * | 6/1998 | Fujiwara et al. | 376/254 |
| 6,542,565 | B2 * | 4/2003 | Ruddy et al. | 376/153 |

* cited by examiner

*Primary Examiner* — Mark R Gaworecki
(74) *Attorney, Agent, or Firm* — John R. Ross; John R. Ross, III

(57) ABSTRACT

A radiation-monitoring diagnostic hodoscope system for producing an approximate image of radiation-detecting components within or external to a pressure vessel of an operating, damaged, or shutdown nuclear-power plant.

21 Claims, 5 Drawing Sheets

RADIATION-MONITORING DIAGNOSTIC HODOSCOPE SYSTEM FOR NUCLEAR-POWER REACTORS

CROSS REFERENCE TO RELATED APPLICATIONS

This application claims the benefit of provisional application Ser. No. 61/632,763, filed Jan. 30, 2012.

FIELD OF THE INVENTION

The present invention relates to radiation-monitoring equipment and systems and in particular to such systems for use at nuclear-power reactors.

BACKGROUND OF THE INVENTION

Of utmost public concern are technologies to improve or ensure nuclear-reactor safety, including means for providing prompt and appropriate corrective measures, especially technologies employed in the low-probability event of severe reactor malfunction, with such ameliorative and supplementary technologies chosen to minimize reactor damage and maximize public safety.

Related to the invention to be disclosed herein is the expired DeVolpi U.S. Pat. No. 4,092,542 issued May 30, 1978, titled "High-Resolution Radiography by Means of a Hodoscope," which illustrates a nonintrusive diagnostic radiographic scanning system for use in nuclear research and development and the expired DeVolpi U.S. Pat. No. 4,649,015 issued 10 Mar. 1987, titled "Monitoring system for a liquid-cooled nuclear fission reactor," which illustrates a stationary nuclear-diagnostic system for monitoring changes of liquid levels in various regions of a water-cooled nuclear power reactor while in normal operation. The above patents are incorporated herein by reference.

Major Nuclear Power Plant Accidents

In more than a half-century of nuclear power, there have been several major accidents at commercial nuclear power plants that resulted in releases of significant or substantial radiation, evacuation of surrounding population, and huge financial costs for cleanup and power-generation displacement.

The Apr. 26, 1986, Chernobyl nuclear accident in the former Soviet Union (now Ukraine) is widely regarded as the worst accident in the history of nuclear power. The reactor was destroyed, over three dozen deaths could be linked directly to the accident, and about 200,000 people had to be permanently relocated after the disaster. Because of the type of reactor (graphite-moderated with interstitial tubes for water cooling) and the nature of the steam-graphite explosion, the extent of damage was so severe as to make the reactor unsalvageable, and it has been permanently enclosed in a specially designed "sarcophagus" to contain external radiation leakage.

On Mar. 28, 1979, a minor malfunction initiated an accident sequence at the Three Mile Island Unit 2 (TMI-2) nuclear generating station near Harrisburg, Pa. During routine maintenance of the secondary coolant side, feedwater to the steam generators was inadvertently interrupted. The water loss caused the primary coolant system to overheat, resulting in an increase in primary-system pressure. A small valve had been opened to relieve pressure in the reactor, but it malfunctioned and failed to close. Lacking direct water-level instrumentation, the operators were not aware that cooling water was draining and events would be initiated that would cause the core to overheat. The instruments that monitored essential conditions inside the nuclear core provided misleading or inadequate information; as a result, plant operators shut down the very emergency water that would have cooled the nuclear core and prevented the subsequent accident.

Although the reactor-protective system automatically scrammed the reactor, it was not in sufficient time to prevent a loss-of-coolant accident and core meltdown. This event has been the most serious commercial nuclear accident in U.S. history, causing fundamental changes in the way nuclear power plants were operated and regulated. The accident itself progressed to the point where over 90% of the reactor core was damaged. No reactor personnel or members of the public received excessive doses of radiation or were injured. It was about five years before it was possible to carry out sufficient nuclear-core diagnostics so as to determine the extent and location of reactor fuel-debris re-concentration, and it required altogether about a ten years for the reactor to be decommissioned and defueled.

After the 2011 Tohoku earthquake and tsunami in Japan beginning Mar. 11, 2011, three reactors at the Fukushima Dai-ichi Nuclear Power Plant underwent loss-of-coolant accidents and core meltdowns. Evacuation, power-displacement, and related costs have been quite expensive and enduring, but no lives were lost as a result of the nuclear accidents. Because of tsunami-induced flood damage to backup reactor-water-cooling systems, improvised backup and emergency systems were not available in time to supply supplementary water cooling in the three reactors so as to prevent the loss-of-coolant accidents. To this day, the degree of fuel re-concentration is unknown in each of the disabled reactors.

A common problem resulting from the loss-of-coolant in the four cited accidents at water-cooled reactors has been the uncertainty and associated potential re-criticality nuclear hazard related to the uncontrolled re-concentration of fuel and debris. In addition, it would have been and remains invaluable to have the capability installed to assess—for the purposes of safe and timely decommissioning—the degree of fuel re-concentration and the level of cooling water maintained inside or outside the reactor pressure vessel, depending on the reactor design.

Hodoscope Nuclear Diagnostics

A hodoscope (from the Greek hodos, for way or path, and skopos, for an observer) is an instrument used to optimally detect radiation and to enhance determination of the radiation trajectory. Typical hodoscopes are comprised of multiple detector-collimating segments arranged in a pattern. As the radiation passes through collimating segments, the detectors associated with these segments record the selected radiation, and this information is then used to infer the direction from which the radiation originated. A typical detector segment is a piece of scintillating material, which emits light when the energy of a charge-producing particle is absorbed in the scintillator The emitted scintillation light can be measured by a photomultiplier tube (PMT) or its equivalent. If the PMT measures a significant amount of light, it can be inferred that radiation passed was absorbed in the scintillator.

A significant design requirement for nuclear diagnostics using a hodoscope consists of arrangements of the collimating and functional elements in such a manner as to minimize extraneous background radiation that might conflict with the desired source of radiation. Other important design requirements relate to spatial and time resolution.

Applicant's U.S. Pat. No. 4,092,542 "High-Resolution Radiography by Means of a Hodoscope," referred to above, teaches that both neutron and gamma digitally-reconstructed radiographs of high spatial resolution are obtained from the hodoscope by the scanning operation of a collimator, by storing detector data outputs, and by rendering computer reconstruction of the data so obtained. The apparatus is adapted to detect fast neutrons, gamma rays, or both, and to use various combinations of the information obtained from fast neutrons and gamma rays to determine what was occurring within the field of view.

Applicant's U.S. Pat. No. 4,649,015 "Monitoring system for a liquid-cooled nuclear fission reactor", also referred to above, illustrates a system for detecting changes in water-coolant levels at various elevations of a water-cooled nuclear power reactor operating at full power. A pre-installed vertical array of gamma-radiation detectors was to be mounted at the inside wall of the reactor biological shield, and the detectors were to be collimated so that each received gamma radiation only from predetermined reactor-vessel elevations and axial positions. No known application is known to have followed from that patent.

The U.S. Pat. No. 4,649,015 was based on applicant's technical analysis that, during normal nuclear-reactor operation to produce steam and thus electrical power, neutrons released in the fission reaction were often thermalized and/or captured: in the water coolant, or in the steel reactor walls, and/or in nuclear fuel or control structures within the reactor vessel. Nuclear-reactor power production results in many neutrons being absorbed in the steel structure and containment, thereby often being converted to gamma radiation having an energy level of the energy range of 5-12 MeV (million electron volts). Meanwhile, neutron capture in water results in a gamma-energy level of approximately 2.2 MeV, while neutron capture in the fission fuel or its cladding mostly provides gamma rays of 1 MeV or less.

Gamma-Ray Detectors

Gamma rays are a high-energy form of penetrating electromagnetic radiation. Gamma-ray photons can be counted individually. While most radiation-detection counters determine only the count rate (i.e. the number of gamma rays interacting in the detector, for example, in one second), a gamma-ray spectrometer also determines the energies of the gamma-ray photons emitted from a source.

Radioactive nuclei (radionuclides) commonly emit gamma rays in the energy range from a few keV to ~10 MeV. Such sources typically produce gamma-ray "line spectra" (i.e., many photons emitted at discrete energies). The boundary between gamma rays and X rays is somewhat blurred, as X rays typically refer to the high-energy electromagnetic emission of atoms, which may extend to over 100 keV, Huge numbers of gamma- and x-ray photons are released in the course of fission processes in nuclear-power plants.

Scintillation Detectors

Scintillation detectors use crystals that emit light when gamma rays interact with the atoms in the crystals. The intensity of the light produced is proportional to the energy deposited in the crystal by the gamma ray. The detectors are joined to photomultipliers (or their solid-state equivalent) that convert the light ultimately into an electrical signal and then amplify the electrical signal. Common scintillators include thallium-doped sodium-iodide (NaI(Tl))—often simplified to sodium-iodide (NaI)—and bismuth-germanate (BGO). Because photomultipliers are also sensitive to ambient light, scintillators are encased in light-tight coverings. NaI(Tl) has two principal advantages: It can be produced in large crystals, yielding good efficiency, and it produces intense bursts of light compared to other spectroscopic scintillators.

The Compton-effect, a form of gamma-radiation interaction, is represented by a continuous distribution at the lower pulse-height regions of the gamma-energy spectrum. The distribution arises because of primary gamma rays that undergo Compton-effect scattering within the crystal: Depending on the scattering angle, Compton-effect electrons have different energies and hence produce pulses in different energy channels. If too many gamma rays are present in a spectrum, Compton gamma-ray distributions can present analysis challenges.

Sodium-iodide detector systems, as with all scintillator systems, are sensitive to changes in temperature. Changes in the operating temperature caused by changes in environmental temperature will shift the spectrum on the horizontal axis.

Semiconductor Detectors

Semiconductor detectors, also called solid-state detectors, rely on detection of the charge carriers (electrons and holes) generated in semiconductors by energy deposited by gamma-ray photons. The arrival of the electron at the positive contact and the hole at the negative contact produces the electrical signal that is sent to the preamplifier, a multichannel amplifier (MCA), and on through the system for analysis. The movement of electrons and holes in a solid-state detector is very similar to the movement of ions within the sensitive volume of gas-filled detectors such as ionization chambers.

Common semiconductor-based detectors include germanium, cadmium telluride and cadmium zinc telluride. Germanium semiconductor detectors provide significantly improved energy resolution in comparison to sodium-iodide scintillation detectors, as explained in the preceding discussion. Germanium semiconductor detectors produce the highest resolution commonly available today, and cryogenic temperatures are vital to their operation.

Principles of Gamma Spectroscopy

The equipment used in gamma spectroscopy includes an energy-sensitive radiation detector, electronics to collect and process the signals produced by the detector—such as a pulse sorter (i,e. a single channel or multichannel analyzer)—and associated amplifiers and data readout devices to generate, display, and store the spectrum. Other components, such as rate meters and peak-position stabilizers, may also be included. The most common detectors in spectroscopy include sodium-iodide (Nap scintillation counters and high-purity germanium detectors.

Gamma-spectroscopy detectors contain passive materials that are available for a gamma interaction to occur in the detector volume. The most important interaction mechanisms are the photoelectric effect, the Compton effect, and pair production. The photoelectric effect is preferred, as it absorbs all of the energy of the incident gamma ray. Full energy absorption is also possible when a series of these interaction mechanisms take place within the detector volume.

The voltage pulse ultimately produced by the detector (or by the photomultiplier in a scintillation detector) is usually shaped by a pre-amplifier and an amplifier. The amplitude of the voltage pulse can be measured and recorded by a single-channel analyzer (SCA) or a multi-channel analyzer (MCA). The analyzers take the very small voltage signal produced from the detector electronic processing system, and convert that analog signal into a digital signal. An analog-to-digital converter (ADC) also sorts pulses by their voltage amplitude. ADCs have specific numbers of "bins" into which the pulses can be sorted; these bins represent the channels in the spectrum, with each channel corresponding to a specific range of gamma-ray photon energy. In a single-channel analyzer, data is recorded for only one channel at a time whereas multichannel analyzers record data for multiple channels simultaneously. The choice for number of channels for the MCA depends on the resolution of the system and the energy range being studied.

The SCA or MCA output is usually sent to a computer, which stores, displays, and analyzes the data. For hodoscope purposes, single channel pulse-amplitude analysis is often sufficient if the detected radiation exceeds a designated energy threshold.

Detector Performance

Gamma-detection systems are selected to take advantage of several detector-performance characteristics. Two of the most important include detector resolution and detector efficiency.

Gamma rays detected in a spectroscopic system produce amplitude peaks in the energy spectrum. The pulse width of the peaks is determined by the resolution of the detector, a very important characteristic of gamma-spectroscopic detectors. High resolution enables energy-separation of two gamma-ray lines that are close to each other in energy. Gamma-spectroscopy systems are designed and adjusted to produce symmetrical peaks of the best possible resolution. The peak shape is usually a Gaussian statistical pulse-energy distribution. For most spectra the horizontal-axis position of the peak is determined by the gamma-ray detection energy, and the area of the peak is determined by the intensity of the gamma ray and the efficiency of the detector.

The most common figure-of-merit used to express detector resolution is full-width-at-half-maximum (FWHM). This is the energy bandwidth of the gamma-ray peak at half of the highest point on the peak distribution. Resolution figures are given with reference to specified gamma-ray energies. Resolution can be expressed in absolute (i.e., eV or MeV) or relative terms. For example, a sodium iodide (NaI) detector may have a FWHM of 9.15 keV at 122 keV, and 82.75 keV at 662 keV. These resolution values are expressed in absolute terms. To express the resolution in relative terms, the FWHM pulse shape in eV or MeV is divided by the energy of the gamma ray. Using the preceding example, the resolution of the detector is 7.5% at 122 keV, and 12.5% at 662 keV. A germanium detector may give resolution of 560 eV at 122 keV, yielding a relative resolution of 0.46%.

Detector Efficiency

Not all gamma rays emitted by a source and passing through the (collimated) detector will produce a count in the system. The probability that an emitted gamma ray will interact with the detector and produce a count is the efficiency of the detector. In general, larger detectors have higher efficiency than smaller detectors, although the shielding properties of the detector material are also important factors. Detector efficiency is measured by comparing a spectrum from a source of known activity to the count rates in each peak to the count rates expected from the known intensities of each gamma ray. "Efficiency," like resolution, can be expressed in absolute or relative terms. Absolute efficiency values represent the probability that a gamma ray of a specified energy passing through the detector will interact and be detected. The energy of the gamma rays being detected is an important factor in the efficiency of the detector.

Radiation detectors may be operated in a "current" mode, in addition to the aforesaid "pulse" mode. In the current mode, pulses are integrated over a time interval such that the output of the detector is a small measurable electrical current, rather than single pulses. Current mode is usually used in situations that involve very high pulse rates and preferably high signal/background ratios.

Calibration and Background

If a gamma spectrometer is used for identifying samples of unknown composition, its energy scale must be calibrated. Calibration is performed by using the peaks of a known radioactive source, such as cesium-137 or cobalt-60. If the channel number is proportional to energy, the channel scale can then be converted to an energy scale.

Because some radioactivity is present everywhere (i.e., background radiation), the gamma spectrum should ideally be analyzed when no source is present. In any event, background radiation must be kept to a minimum and its effects subtracted from the actual measurement. The heavy-element lead and other high-density absorbers can be placed around the measurement apparatus to reduce background radiation.

Monitoring Reactor Parameters

Several different types of internal, intrusive monitors are used or have been proposed for measuring reactor functional properties such as (1) water pressure, (2) fuel temperature, and (3) neutron fluxes. With internal monitors, such detectors are positioned within the reactor vessel, while the readout devices are located outside of the reactor vessel. Conduits must therefore be used between the detectors and their readout devices, and these conduits must pass through penetrations in the reactor vessel itself and possibly through other pressure-boundary structures; these requirements constitute a major drawback to internal monitors.

Another major drawback for internal monitors is the uncertainty associated with survival during an accident of a detector located within the confines of the reactor vessel, especially if the cause or effect of the accident that might be responsible for a change in measured conditions in the first place.

Furthermore, pressure monitors are comparatively insensitive in distinguishing between water and water-steam mixtures. Moreover, in-core neutron flux detection has heretofore been of limited precision in monitoring water level inside the vessel.

External monitors are also available, whereby the detector and readout device are located outside of the reactor vessel, thus eliminating the drawbacks of internally located detectors. One such external control is known as a source-range or low-intensity neutron detector. Such a detector is designed to respond to low start-up power levels, perhaps 1-10% of full output power. Although typical source-range monitor output signals vary with changing water levels in the reactor vessel, its time resolution, especially at full-power levels, is too poor to advise of the water level in the reactor with sufficient reliability and accuracy.

Prior-Art Gamma Detector for Reactor Water-Level Monitoring

U.S. Pat. No. 4,649,015 describes how exterior components can handle the output signals from a gamma detector.

See FIG. 8 (FIG. 9 of the U.S. Pat. No. 4,649,015), where detectors 50 (including a signal processor 52), a digital data recorder 54, a data analyzer 56, and a graphical output display 57 are utilized in the system. The collimated-detector signals over time can be counted and analyzed by computer techniques. The adjacent detectors of the same set would have related outputs for similar water conditions, and the ongoing signals of each detector would be compared against its past signals and against the concurrent signals of the normalizing and adjacent detectors so as to detect transitions when the water level or density may change during operation.

The changing detected signals from adjacent like detectors would indicate the presence of the water level at some precise proximate location. If the presence of water caused neutron capture in the reactor pressure vessel, the gamma transmission and detection would be low. However, should the water be voided at a particular location—within the reactor vessel, the vessel, downcomer, or core itself—the neutron capture in the pressure vessel would produce higher intensities of gamma radiation of the 5-12 MeV range. Regions of greater or lesser changes in detector response would typically be located near and above the liquid surface.

Prior Nuclear-Diagnostic Monitoring Equipment and Methods

In research and power reactors, external instruments have sometimes been used for determining certain operational characteristics. Previous art relevant to the present invention has been directed at obtaining the following types of real-time in-vessel information: core and coolant temperatures and/or pressures, coolant-water levels or loss-of-coolant, nuclear-reactor safety or fuel-element failure, nuclear-core integrity or loss of integrity, fissile-fuel distribution or redistribution. All of these have been and can be based on instruments that are located within the reactor pressure vessel, and thus such instruments are subject to damage prior to or during an accident.

In view of these said limitations, especially needed for improved reactor safety and operation are instruments that can be securely located and operated outside reactor pressure vessels in order to provide real-time and post-shutdown monitoring of essential reactor parameters and of functional conditions that occur inside the reactor vessel.

SUMMARY OF THE INVENTION

The present invention goes beyond Applicant's inventions described in his two patents referenced above. The present invention provides a broad range of relevant normal and emergency nuclear-diagnostic functions for both operating and non-operating reactors, including reactors that have been damaged, shut down and/or are being decommissioned. The present invention also applies specifically to the three Fukushima Dai-Ichi boiling-water nuclear reactors that suffered nuclear meltdown as described above.

The difficulties and malfunctions experienced at Fukushima Dai-ichi nuclear-reactor plant illustrate the need for one or more radiation-monitoring diagnostic hodoscopes of the present invention at the Dai-ichi nuclear station, at other reactor stations in Japan, and at other operating reactors in the world:
  (1) in order to prevent or minimize further harmful effects from damaged reactors,
  (2) in order to assist the safe and economic decommissioning or repair of damaged reactors, and
  (3) to assist in the orderly restart of undamaged reactors.

If preferred embodiments of this radiation-monitoring diagnostic hodoscope invention had been installed prior to the reactor accidents, the internal damage might have been greatly reduced. But even now, implementation of certain aspects of this invention at the Fukushima nuclear plant would help reduce the hazards, time delay, and cost for decommissioning the damaged reactors and would allow earlier return to operation of the undamaged reactors at the same site.

Also, the invention can be retrofitted to other liquid-cooled nuclear reactors operating throughout the world in such a manner that the nuclear-diagnostic equipment can be prepositioned for use during normal reactor operation, as well as to be used under the type of post-accident conditions that prevailed at TMI-2 and Fukushima.

The present invention provides a unique means—in particular, but not exclusively—of nondestructively determining coolant-water level and core-fuel distribution or redistribution in reactors that have been shut down deliberately or by accident, including specifically the Fukushima Dai-Ichi boiling-water-type reactors. Making use of the art described in the two expired patents referenced above, improvements provided by the present invention combine and apply directly to the configuration and circumstances such as those of the damaged and undamaged reactors at the Fukushima nuclear power station.

This invention fulfills a technical challenge that has yet to be surmounted for the Japanese reactors, and is yet to be recognized or implemented for liquid- or gas-cooled nuclear-power reactors around the world.

Preferred embodiments of the present invention include a radiation-monitoring diagnostic hodoscope system for producing an approximate image of gamma-radiation-producing components of a pressure vessel of a damaged or otherwise shutdown nuclear plant. As used herein and in the appended claims the word "image" in this context includes any description, graphical, verbal or otherwise, that describes the location of substantial concentrations of the above gamma radiation producing components. This includes one-dimensional, two dimensional and three dimensional graphical descriptions. The word "image" also includes a verbal description of substantial and unusual fission product concentrations at the bottom of the pressure vessel or below the pressure vessel. These embodiments include at least one gamma-radiation-monitoring hodoscope unit adapted to detect gamma radiation in a limited substantially straight narrow radiation beam typically of less than 10 degrees and in at least one specific gamma-energy range. Each hodoscope unit includes a collimator to produce the narrow radiation beam and a radiation detector for producing electrical signals corresponding to intensities of gamma radiation in the at least two specific gamma energy ranges. The system includes a technique for positioning the one or more hodoscope units so as to accumulate sufficient gamma radiation data representing radiation intensity and gamma energies in a sufficiently large number of narrow radiation beams to create the approximate three-dimensional reconstructed image of gamma radiation-producing sources within, below or near said pressure vessel. The preferred embodiments also include a computer processor programmed with an algorithm associating the radiation data so as to produce the approximate two-dimensional or three-dimensional image reconstruction of said radiation-producing components.

The parallel or simultaneous detection of neutron radiation, as appropriate, is also to be included within the embodiments of this invention.

Each of the manifestations described in this invention provides its own benefits, context, and limitations, such that each embodiment complements and supplements the other in providing essential or useful data that assists safe and efficient decommissioning of damaged reactors and in supporting preventative-safety for undamaged reactors of the same type. This present invention introduces concepts that apply specifically to a reactor that has been shut down under either normal or abnormal circumstances, and no longer engaged in power production.

It is important to note that the occurrence and rate of neutron capture inside the reactor are altered significantly when the level or density of coolant varies at any water, air, or structural interface, even if the reactor nominally has been deliberately or unavoidably shut down and no steam is being generated to produce electrical power. Comparative diagnostic analysis of the radiation-monitoring hodoscope detector data is capable of identifying radical changes from the normal condition, such as the presence or absence of liquid coolant, and of recognizing changes in the density of the coolant at these specific regions due to bubbles or steam.

In considering potential applications of the present invention, it is noted that there is substantial lingering uncertainty regarding the damaged Fukushima reactors, as to the height, location, and concentration of water coolant in the reactor pressure vessel and in its external containment vessel. At the same time, there is considerable and crucial safety-related uncertainty as to the distribution or redistribution of fuel and structural components in the damaged reactor cores and other components within the pressure vessels. Obtaining detailed knowledge of these factors is vital to the safety, cost, procedures, and duration for decommissioning the reactors.

The present invention utilizes one or more gamma-radiation detectors with a collimator technique that functions so as to sense separate regions within the reactor vessel, thus providing unique signals for these respective regions, whereby comparative analysis of these signals can be used to advise of the presence and density of cooling water in the vessel. The present invention goes further than application to prior art expired patents by also advising of the presence, density, and redistribution of reactor-core materials in the reactor pressure vessel or its immediate surroundings within the freestanding steel dry well of a boiling-water reactor when the reactor is no longer deliberately generating steam for electrical power.

Preferred embodiments of the present invention provide an ordered and considered grouping of detectors similar to Applicants' U.S. Pat. No. 4,649,015, which provided "a plurality of gamma radiation detectors arranged vertically along the reactor vessel itself, and collimator means for each detector to limit the detection of gamma radiation from only isolated regions of the vessel, where the detectors cumulatively provide sufficient readout signals from the entire reactor vessel vertically and radially at specific regions in the reactor vessel [such] that comparative analysis of these readouts yields precise indications of the water level and water density therein, all independently of the power level of the reactor." The invention covered by that patent was based on the observation that variation in the density of coolant produced a substantial change in spectrum and intensity of gamma radiation emanating from steel and other materials within the reactor. However, damaged reactors that are no longer operative—such as those at Fukushima—do not generate radiation source levels that would provide sufficient real-time signal strength as required for the invention to be functional as described in U.S. Pat. No. 4,649,015. On the other hand the present invention is tailored to be functional in a reactor that has been shut down for hours, days, months, and years. The present invention overcomes inherent flux-dependent fuel-concentration sensitivity reductions by detecting residual gamma-radiation emission resulting from delayed and spontaneous fission in fissionable fuel, as well as residual gamma-ray emissions from fission products in the reactor core, or residual gamma-ray emission from material redistributed within or external to the reactor pressure vessel by the loss-of-coolant accident.

Even though the steel walls of the reactor pressure vessel are of considerable thickness (typically 15-20 centimeters), energetic gamma radiation has a relatively high probability of penetrating the reactor vessel. Thus, residual radiation associated with the reactor fuel and other core structure contributes to a continuum flux of gamma rays at lower energies that can be detected external to the pressure vessel and external to the biological shield.

The present invention relies partly on some neutronic and radiation phenomena, as well as instrument functions as in U.S. Pat. No. 4,649,015, but this invention makes use of new technical insight and analysis to the effect that:

(1) radiation associated with nuclear fuel, consisting of intermediate-energy gamma rays, will contribute a detectable signal that distinguishes radiation associated with the coolant water, and importantly differentiated from background radiation at lower energy levels, and (2) modern gamma-ray detector systems and their multichannel data storage and analysis provide more useful, sensitive, and specific diagnostic information than previously available, and (3) neutron and gamma radiation emerging from the reactor provide a hodoscope nuclear-diagnostic source term for determining a variety of useful or essential parameters relevant to the safety and operation of power reactors before, during, or after shutdown.

Efficient detection and energy sorting of gamma rays can be accomplished in standard thallium-activated sodium-iodide or bismuth-germanium-oxide scintillation detectors. For water-cooled reactors, essentially all excess neutrons (produced by the fission reaction) that do not leak out of the pressure vessel will be thermalized and captured in the water or steel within or part of the vessel, thus producing telltale detectable gamma emission which can be distinguished by sensitive gamma detectors Specific embodiments of this invention include radiation-monitoring multichannel diagnostic hodoscopes. One embodiment comprises a single-channel hodoscope. This embodiment can be mounted of a robotic system for remotely positioning the hodoscope so as to view the pressure vessel and the region around and below the pressure vessel from a variety of positions. Another embodiment is in the form of an array of gamma-ray detectors embedded within the reactor biological shield; this embodiment is designated an embedded-hodoscope system. Another embodiment is in the form of a movable array of gamma-ray detectors that can be positioned into and remotely operated within the reactor containment building; this embodiment is designated the movable-hodoscope array system. This embodiment can also be mounted on a robotic device that is controlled remotely.

The embedded-hodoscope system can also function to monitor coolant level and density, as well as fuel-related distribution and various reactor operational and process parameters, during operation and immediately after or long after shutdown.

DETAILED DESCRIPTION OF PREFERRED EMBODIMENTS

Figure 1:
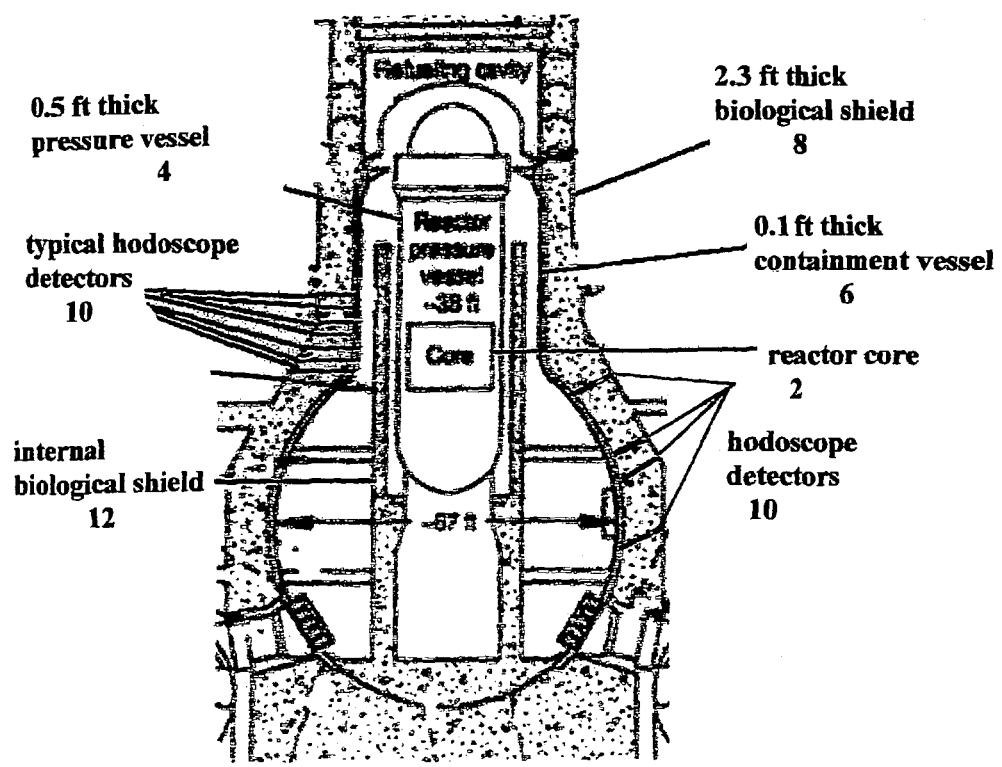
FIG. 1 is an elevation cutaway sketch of a Fukushima-type boiling water reactor, indicating features significant to this invention.

As indicated in FIG. 1, which is a schematic cutaway view of a typical boiling water reactor similar to the Fukushima boiling water reactors, the nuclear core location 2 (dotted area) is shown relative to other major components. The reactor core 2, in an intact configuration, consists primarily of nuclear fuel rods and water coolant, along with essential structural and operational elements that control and assist the production and transfer of heat from the fuel rods to the circulating water coolant.

The reactor pressure vessel 4 is made of steel with a typical thickness of about 16 centimeters, completely surrounding the reactor core 2, water coolant, and other internal structures. In the Tsunami-affected Fukushima reactors, components of the nuclear core 2 could have been damaged or become molten, thus being redistributed throughout the reactor pressure vessel 4, most likely falling downward under the effects of gravity and other causes, possibly exiting the pressure vessel and falling down upon the concrete pedestal known as the core catcher. Thus, the range of application for embedded hodoscope detectors might be the full volume, elevation and diameter, of the reactor pressure vessel 4 and extend downward to the concrete core-catcher pedestal.

Figure 2A:
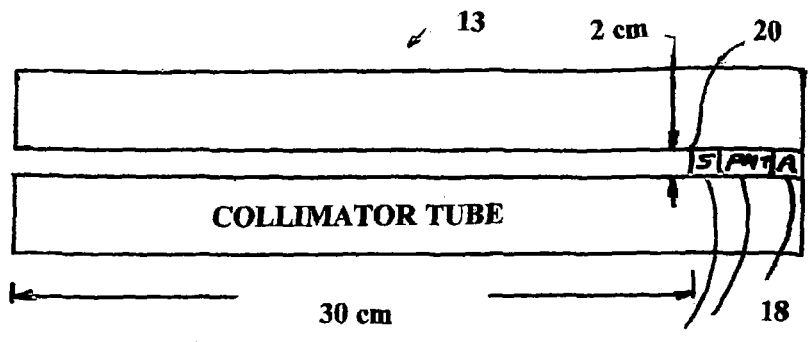
FIGS. 2A and 2B are drawings of a single-channel hodoscope that is illustrated with a tungsten-tube collimator.
Figure 2B:
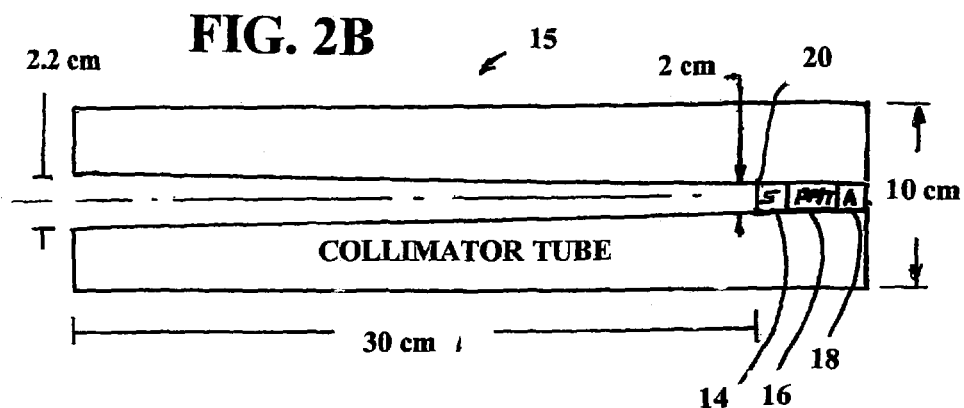

The external reactor containment vessel 6, made of steel with a thickness of about 3 centimeters, and the conforming primary biological shield 8 comprised mostly made of concrete with a thickness of at least or about 69 cm. In preferred embodiments, an array of single-channel collimating hodoscopes, similar to the hodoscopes shown in FIGS. 2A and 2B, is shown as 10 in FIG. 1 at a variety of elevational locations in penetrations through the biological shield 8. However, when the hodoscopes are mounted within the concrete structure of the biological shield, the collimating element can be much thinner than the collimating elements shown in FIGS. 2A and 2B, or in some cases the concrete itself may serve as the collimating element. These hodoscopes are preferably designed to fit in existing penetrations or in penetrations having diameters (such as 1.3 cm) that can be easily drilled through the concrete. An internal biological shield 12, that does not necessarily fully surround the reactor pressure vessel 4, is made of concrete with a thickness of about 70 centimeters. The components shown in FIG. 1 are all contained in an external containment building not shown in FIG. 1 but shown at 7 in FIG. 5.

Preferred First Embodiment

Single-Channel Hodoscope

FIGS. 2A and 2B show some essential features of two versions (13 in FIGS. 2A and 15 in FIG. 2B) of a single-channel hodoscope of the present invention. The FIG. 2A version includes a thick, long tungsten (lead or steel could be substituted) collimating tube having a 2-cm channel drilled through the center of the tube.

At the end of the tube is installed an off-the-shelf gamma scintillation detector, such as Model 943-37 available from Fluke Biomedical with offices in Everett, Wash. This model is 5 cm in diameter and includes a 5-cm long sodium iodide (NaI) crystal 14, a photomultiplier tube assembly 16 and a preamplifier 18. Mounted in front of the detector is a thin lead and/or cadmium filter, the position of which is shown at 20, used to block low-energy neutrons and gamma-ray background. This channel limits the field of view of this specific hodoscope to about 4 degrees. In the unit shown in FIG. 2B, the collimating channel is tapered to provide a field of view of slightly more than 6 degrees. Preferably the field of view of the single-channel hodoscope should be kept within 10 degrees. In some preferred embodiments the field of view could be restricted to less than 4 degrees as shown in FIG. 2A by making the channel longer or tapering the channel in a direction opposite that shown in FIG. 2B.

Figure 6:
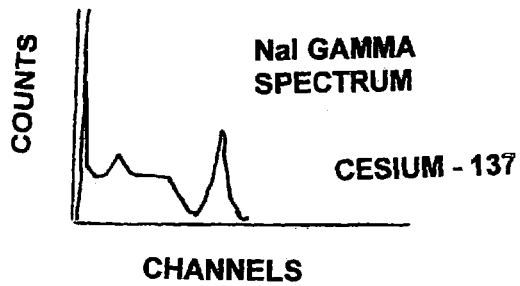
FIGS. 6 and 7 are examples of NaI gamma spectra for Cs-137 and Co-60.
Figure 7:
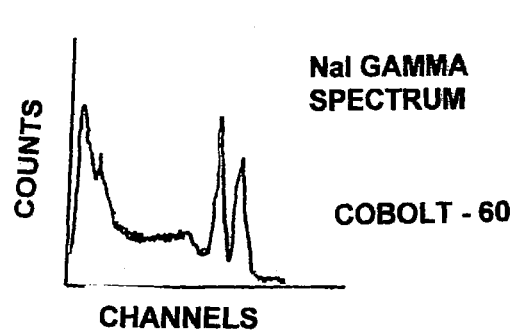
Figure 8:
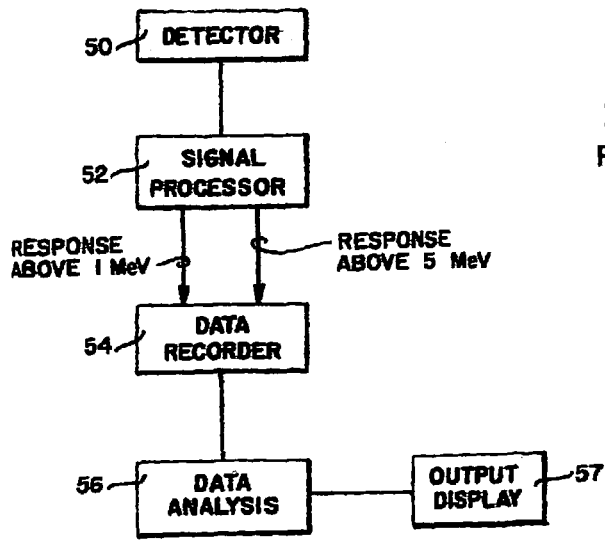
FIG. 8 diagrams a standard technique for data collection from the Applicant's U.S. Pat. No. 4,649,015.

In this preferred embodiment, Applicant has chosen to utilize a NaI-based radiation detector. FIGS. 6 and 7 show examples of calibration results that can be expected from the use of a NaI scintillator. FIG. 6 shows a typical cesium-137 spectrum from an isolated radioactive cesium source and recorded with a typical NaI spectrometer. FIG. 7 shows a typical Cobalt-60 spectrum from an isolated Cobalt-60 radiation source and recorded with a typical NaI spectrometer. Cesium-137 is a fission product with a half life of about 30.2 years and decays with a 32 KeV x-ray peak and a 662 KeV gamma-ray peak. Cobalt-60 has a half life of about 5.27 years and decays with two gamma-ray peaks at 1173.2 KeV and at 1332.5 KeV.

Both Co-60 and Cs-137 radioactive isotopes are expected to contribute significantly to the radiation emitted from a reactor core that has been shut down for about two years. In preferred embodiments it would be important to be able to distinguish the radiation produced by such sources so as to determine where the fission products are located as a strong indication of the location of the reactor core materials.

Figure 2C:
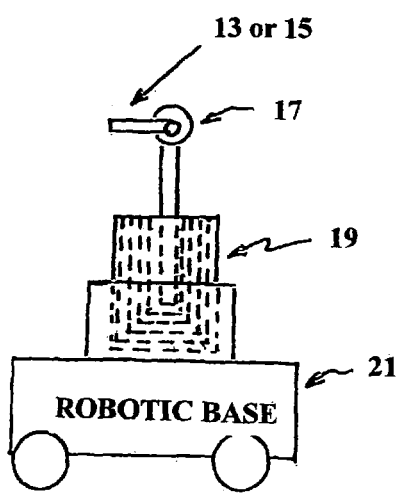
FIG. 2C shows a mobile-hodoscope mounted on a robotic transport system.

A single-channel hodoscope of the type described above—if used in very high radiation environments—could be utilized as a part of a robotic system. An example is shown in FIG. 2C. This system includes the single-channel or multi-channel hodoscope 13 or 15, a two-axis gimbal 17 for pointing the hodoscope 360 degrees in horizontal and about 120 degrees in elevation, a telescoping support 19 to position the gimbal vertically, and the above components are mounted on a robotic base 21. All of these components should be designed to be remotely controlled. In preferred embodiments a camera and a visible light source (not shown) could be bore-mounted on the hodoscope so that visible images of the reactor structures can be recorded simultaneously with the radiation data.

Second Preferred Embodiment

Embedded Hodoscopes

Figure 3:
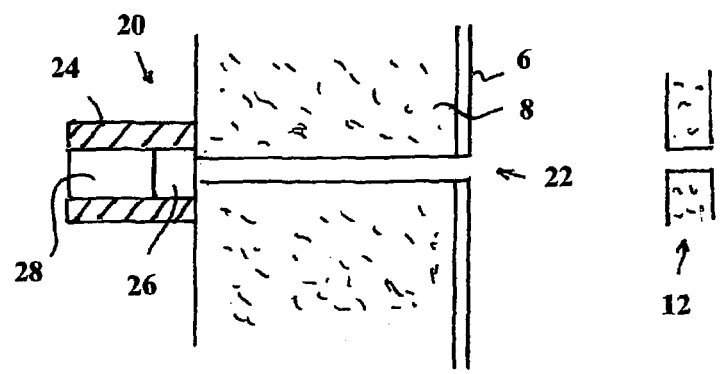
FIG. 3 is a side view of a typical embedded-hodoscope detector of the present invention.

FIG. 3 is a side view of a typical embedded hodoscope detector 20 of the present invention. A slotted collimating channel 22, with a typical diameter of 5 cm is drilled through the 40-centimeter steel external reactor containment vessel 6 and the 320-centimeter concrete biological shield 8 and the internal biological shield 12. A shielding sleeve—made of lead, steel, or tungsten—may be formed around the channel 22. A radiation barrier 24 preferably made of tungsten, lead or steel that shields a sodium-iodide (thallium-activated) scintillation crystal 26. A cavity adjacent to crystal 26 contains electronic preamplifiers or other electronics 28. This embodiment with its thalium-activated sodium-iodide crystal does not necessarily need refrigerant. The collimating channel 22 could be a pre-existing instrument access hole or a newly drilled or enlarged hole through the concrete biological radiation shield. In some embodiments, channel 22 would not be drilled through the steel reactor containment vessel liner 6. A multiplicity of such holes, at different elevations and different radial positions, each with embedded hodoscope detectors 14, would allow three-dimensional numerical reconstructions of reactor fuel and water coolant configuration within or outside the reactor pressure vessel 4 of a damaged reactor.

Another arrangement of detectors could be as in the previously described Applicant's U.S. Pat. No. 4,649,015 for a monitoring system for a liquid-cooled reactor, such that the collimated detectors are pre-installed in the space between the reactor pressure vessel and the biological shield, and are used for purposes not proposed or claimed in that patent, but now specifically claimed in this present patent application.

A design-basis objective for this present embodiment might require that both horizontal and vertical fields of view of the embedded hodoscope detector array overlap so as to provide comparatively uniform and thorough two- and three-dimensional image-reconstruction that spans the reactor pressure vessel 4, its internals, and its internal or external core-catcher region, especially for a reactor with a damaged core.

Another design-basis objective of this present invention is for the detectors to be pre-installed in liquid-cooled reactors in order that the detector array might be in place and used to measure fuel redistribution in the case of an accident.

A further design-basis objective of the present invention is to be pre-installed in liquid-cooled reactors in order that the detectors might be used to monitor various reactor operating, safety, and process parameters that might be inferred from neutron and gamma fluxes measured in said hodoscope detectors designed for both neutron and gamma detection, in accordance with the claims of this present application.

Third Preferred Embodiment

Movable Hodoscope Array

Figure 4:
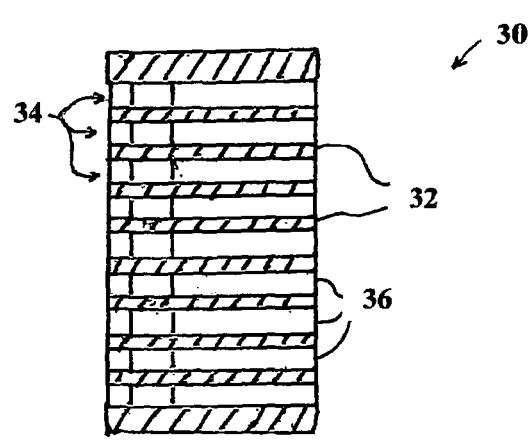
FIG. 4 is a side view of a typical movable-hodoscope detector array of the present invention.

FIG. 4 which is a side view of a movable hodoscope detector array section 30 consisting of hodoscopes of the present invention arranged in a vertical array. Each hodoscope comprises a collimating channel 36 with a typical diameter of 1.3 cm. This collimating channel 36 serves to limit the entry cone for radiation which impinges on the detector inserted at the end of that channel. This collimating function is crucial for reducing the entry of extraneous background radiation that emanates from portions of the pressure vessel or reactor outside the angular view of any specific collimating channel.

A major aspect of this invention is the multichannel use of a multiplicity (array) 30 of such mobile collimating detectors, in order that triangulation could take place, enabling computer-aided reconstruction of the reactor fuel and coolant configuration that is responsible for the detected radiation source.

Lead, tungsten, or steel shielding effectively and simultaneously collimates and shields radiation allowed into the detector 34. This shielding is necessary to minimize the amount of stray radiation that enters into the collimated detector 34; such extraneous radiation might compete by providing either conflicting pulses in the energy range of interest or too many low-amplitude pulses that overcome the instrument data processing circuits.

Each radiation-monitoring detector 34 in the movable hodoscope array 30 preferably consists of a gamma detector, such as a thallium-activated sodium-iodide scintillator. The choice of detector 34 usually involves technical and economic tradeoffs in radiation energy sensitivity and saturation count rate. The choice is often made before the final system is installed on the basis of expected detector energy-dependent count rate, confirmed by preliminary measurements. Other factors which come into play are the contemporaneous strength of the time-dependent source term, the time-resolution sought, as well as dynamic range. A variety of radiation detectors are discussed in the Background section of this specification.

As in the case of each of the other embodiments, neutron detectors could be used instead of, or in combination with, the gamma detectors under appropriate conditions.

A cavity is provided adjacent to the detector 34 in which any necessary electronic preamplifiers or other electronics are positioned. This arrangement will depend on the type of detector chosen. It is significant for this invention of the movable hodoscope detector array 30 represented in FIG. 4 that there be a multiplicity of collimated detectors, in this example nine channels.

In this example, the nine channels are arranged vertically in a manner that is capable of providing a design-basis vertical spatial resolution at the targeted area within the field of diagnostic view. The vertical spacing between detectors and the number of installed detectors are determined by design-basis factors such as engineering constraints, materials availability, system cost, and reactor accessibility. The number of detectors and their vertical spacing are factors in determining the corresponding spatial resolution for reactor fuel and coolant in the field of view.

The movable hodoscope detector array 30 depicted in FIG. 4 is shown as a one-dimensional vertical array; however, to improve spatial resolution and reduce data collection time, the array can be expanded so as to have more than one vertical array of parallel channels arranged on a common horizontal plane to reduce the time needed to record needed data.

An essential operational factor associated with this movable hodoscope detector array 30 is a functional ability to adjust the position and orientation of the array under remote control. Forward and backward movement on the horizontal plane will affect the detected radiation flux. Angular traverses on a single horizontal plane will increase the spatial resolution and range of detection. Spatial and material resolution of reactor fuel segments and reactor coolant level can be optimized by tradeoffs in horizontal scanning increments and counting time.

Because measurements made by a movable hodoscope detector array are made simultaneously in all detector channels, it is possible to create overlapping data results through a horizontal and/or vertical scanning operation that self-calibrates the array, thus achieving spatial resolution much better than the inter-channel distance between collimated detectors.

A factor associated with this movable hodoscope detector array depicted in FIG. 4 is a functional ability to adjust the position and orientation of the array under remote control. Angular traverses on a single horizontal plane around the reactor may be utilized to increase the spatial resolution and range of detection. Spatial and material resolution of reactor fuel segments and reactor coolant level can be optimized by tradeoffs in horizontal or vertical scanning increments and counting time.

The movable hodoscope detector array 30 is intended to be reliably transported, centrally positioned, and remotely operated within the reactor building and within the reactor external containment vessel.

The collimating channels 36 with a typical diameter of 2 cm might be used as shown in FIG. 4. A typical movable hodoscope detector array 30 of the present invention, may be positioned inside the reactor containment building 7 but outside the external reactor containment vessel 6 and secondary shield, and in such a position as not to be occluded by the internal biological shield 12. Half of the internal biological shield 12 is made of concrete with a typical thickness of about 70 centimeters but does not necessarily fully surround the reactor pressure vessel 4.

Figure 5:
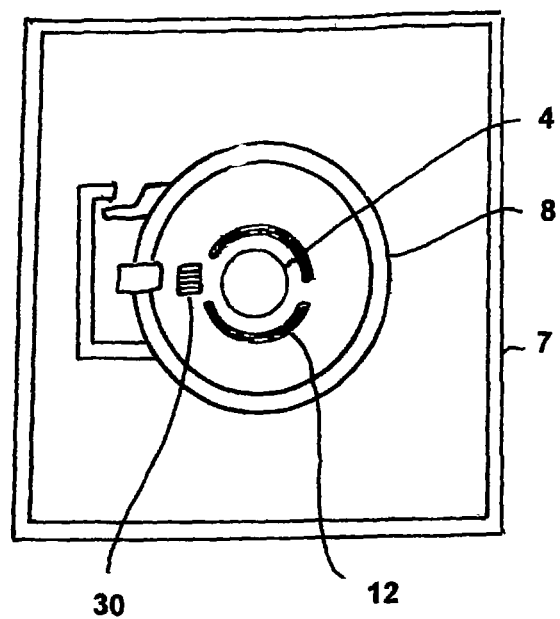
FIG. 5 is a top schematic view indicating a location for the typical movable-hodoscope detector array of the present invention.

The movable-hodoscope detector array 30 should preferably be constructed in such a manner that it can be assembled and tested elsewhere, moved to the reactor, introduced through the enclosure on to the reactor floor position indicated in FIG. 5 by robotic devices, and be positioned and operated by remote means. Also indicated in FIG. 5, there is a portal region through which the movable-hodoscope detector array 30 can be positioned to directly view the reactor core 1, without line-of-sight interference from any two-part reactor biological shield 12. A design-basis objective for the movable-hodoscope detector array 30 might be to provide as much vertical and horizontal field-of-view coverage as to encompass the entire reactor pressure vessel.

A major aspect of this embodiment is a system of at least two hodoscopes such as those described above but so arranged that triangulation to take place enabling computer reconstruction of the reactor fuel and coolant configuration.

Applications of the Present Invention

Two initial and most imminent practical and needed applications for this invention are intended for the damaged Fukushima nuclear-power-station reactors in determining post-accident spatial reconfiguration of both reactor fuel and coolant. For these two specific objectives, there are two separate and complementary embodiments of this invention—which depend on the degree of access available in the reactor building—that enable external diagnostic interpretation simultaneously of both fuel and coolant configuration or reconfiguration resulting from an internal nuclear core accident.

A third application for this invention is specifically intended for the remaining boiling-water reactors in Japan, the intention being to provide real-time coolant water-level monitoring, during operation as well as while undergoing startup or shutdown, thus potentially averting the same type of the coolant-level uncertainty experienced by the earthquake- and tsunami-impacted Fukushima Dai-Ichi boiling-water reactors.

A fourth application for this invention in operating water-cooled reactors around the world is to pre-install a backup instrumentation system that will provide real-time water-level monitoring for any abnormal event in which operational problems might occur similar to those that happened at Fukushima nuclear-power station and the TMI-2 reactor. In this respect, application is similar to Applicant's U.S. Pat. No. 4,649,015, except that the equipment would be pre-installed so as to be in place for use in case fuel-distribution measurements were needed as a result of a loss-of-coolant induced fuel meltdown. The range of vertical coverage for the sole purpose of U.S. Pat. No. 4,649,015 is limited to the vertical mid-range near the reactor core; the range of coverage for fuel redistribution necessarily requires detectors vertically situated below the core and even below the pressure vessel in the case of some reactors. Thus, axial overlap between the two inventions is only in the core region.

A fifth application for this invention is primarily designed to be used in liquid-cooled power reactors for monitoring the coolant levels in the reactor vessel; but it could be retrofitted into existing reactors with the radiation-monitoring hodoscope detectors being located adjacent to the reactor vessel, inside the biological shield if space permits. In this role, the detectors focused on the vertical midplane of the reactor might be identical to those other detectors installed for the other herein listed applications.

A sixth application for this invention, in case of an accidental or emergency shutdown of a liquid-cooled nuclear reactor, is to provide backup instrumentation pre-positioned and functional for determining and monitoring the configuration or reconfiguration of coolant and fuel inside or outside the reactor pressure vessel.

A seventh application for this invention is for independent, external monitoring of reactor process and safety parameters that can be inferred from the measurable gamma and neutron fluxes incident on the embedded hodoscope array.

The embodied radiation-monitoring diagnostic hodoscope system will have sufficient sensitivity to provide relevant information at full reactor power and it will have adequate sensitivity for observation at decay-heat levels in the event of reactor shut down or accidental disablement. Moreover, the embedded-hodoscope system is positioned entirely external of the pressure boundaries of the reactor vessel and thus have substantial durability and be immune from destruction or inoperative condition caused by deliberate or uncontrolled water level changes, reactor-core overheating, or internal reactor-fuel redistribution. It should also be self-actuated and have independent internal electrical-power sources.

Inter-calibration of both embodiments is accomplished by using radiation sources of known comparative intensity and appropriate energy, with particular reliance on comparatively long-lived radioactive cobalt-60. In the case of the embedded gamma detectors, a low-intensity calibration cobalt-60 source could be permanently affixed adjacent to each embedded detector. In the case of the movable-hodsoscope array, the entire gamma-detection assembly could be intercalibrated by moving a single cobalt-60 source in front of each detector, one by one. Such calibration measures greatly enhance the functional stability and spatial resolution of hodoscope detectors.

Calculations for the use of detectors of the hodoscope type suggest that horizontal liquid-level resolution of perhaps 10-20% of the spacing between adjacent detectors would be possible. By appropriate vertical detector spacing—every 100 centimeters for example—the vertical resolution could be definitive to within 10 to 20 centimeters. For a shutdown reactor, the spacing intended for water-level monitoring would be adequate for post-accident measurement of fuel redistribution.

In order for embedded hodoscope detectors to remain dependable for long-term operation under ordinary and extraordinary conditions within the reactor containment building, the electronic modules and signal processing for each hodoscope detector would have to have design features that provide a wide dynamic range, that have built-in system redundancy, that are capable of high radiation endurance, and that have independent and long-lasting backup power in case of system-wide electrical-supply loss.

A major feature of this invention is an improved ability to distinguish radiation emitted by the reactor fuel, in contrast to radiation from other sources. Such extraneous gamma radiation from other sources generally have lower emission energies compared to that originating from fuel. By setting a high gamma-energy electronic bias, it normally becomes possible to limit sensitivity primarily to the radiation signal coming from fuel.

Finally, depending on the amount of intervening material, it will be possible to directly detect or diagnostically infer the presence of nuclear fuel at any given reactor elevation and radial location. This diagnostic determination would be based on being able to distinguish lower-energy gamma rays emitted preferentially from delayed fission and capture processes that occur directly within the fuel, whether the fuel is intact or redistributed.

Ex-Vessel Hodoscopes as Operating and Process Instruments

The use of hodoscope ex-vessel array of neutron and gamma detectors to infer other process or operating nuclear-reactor parameters, such as water temperature, water pressure, and reactivity in real-time or a-postiori. The neutron and gamma detectors would function in such a manner as to store on-line all energy- and rate-dependent information accumulated during or after reactor operation, and such information could be process either on-line or off-line to derive functional parameters of the operating reactor.

A standard nuclear-power-reactor instrument and control system senses basic physical parameters, monitors performance, integrates information, and makes automatic adjustments to plant operations to keep process variables within the plant design limits. By reacting appropriately to failures and abnormal events, the standard nuclear-reactor instrument and control system ensures the plant's safety and efficient production of power. The said ex-vessel hodoscope monitor of neutron and gamma fluxes enhances the safety, reliability, and production of power.

The standard reactor instrument and control system performs four basic functions: (1) obtains accurate and relevant information to make the appropriate actions during normal as well as abnormal operation; (2) provides the capacity to exercise automatic control over the plant and its associated systems; (3) enables actions needed to maintain efficient and safe operation; and (4) serves the critical function of protecting the plant from faults in the system or errors made by the operator as well as the effect of abnormal or extreme external events that threaten the plant's operation. The standard system should enable the plant to operate safely for an extended period without operator intervention following an accident. The said external monitor of neutron and gamma fluxes can assist in the performance of the basic functions so as to enable appropriate actions during normal and abnormal operation, reduce operator errors, and enable safe operation following an accident.

Standard nuclear-plant instrument and control systems must be accurate to properly sense and communicate the process variables and have reasonably fast response to provide timely display, adjustment, and protection against upsets in both the main plant and its ancillary systems, and the standard reactor instruments require greater redundancy and reliability in plants-control infrastructure. Standard nuclear-plant surveillance and diagnostic systems must also monitor sensor signals for abnormalities. The said external monitor of neutron and gamma fluxes provides information redundancy and assists in monitoring conventional sensor signals for abnormalities.

Standard nuclear plant instrumentation can generally be classified into the following categories: Nuclear instruments that measure nuclear processes or reactor power, such as neutron flux density; process instruments that measure non-nuclear processes such as reactor pressure, coolant or pressurizer level, steam flow, coolant temperature and flow, and containment pressure; and radiation monitoring instruments that measure radiation outflow. Standard reactor sensors interact with the plant's physical processes to measure operational-process variables as well as control, regulation, and safety components that process the sensors' data. The said external monitor of neutron and gamma fluxes directly measures the outgoing neutron and gamma flux density, thus indirectly indicating non-nuclear reactor-process parameters such as pressure, coolant level, steam flow, coolant temperature and flow, and internal pressure.

The most important and safety-critical measurements for the control and safety protection of nuclear reactors are temperature, pressure, level, flow, and neutron flux. Such standard sensors normally reside in the harsh environment of the in-vessel reactor-radiation field. The said external monitor of neutron and gamma fluxes resides outside the harsh environment of the in-vessel radiation field.

Standard reactor instrumentation and control systems ensure the nuclear plant's safety and efficient production of power by reacting appropriately to failures and abnormal events. The external monitoring of neutron and gamma fluxes adds substantial, independent, safety-redundant instrumentation to continuously monitor plant safety and power-production efficiency. In preferred embodiments, hodoscope channels are mounted in the biological shield as shown in FIG. 1.

Alternative Gamma Detectors

A large variety of gamma ray detectors are available off-the-shelf that can be utilized in hodoscopes as described above, These include scintillator detectors of various types including the NaI detectors as described in detail. These detectors typically include a photomultiplier tube or a photodiode that absorbs light emitted by the scintillator and reemits in the form of electrons via the photoelectric effect. An alternative to the photomultiplier tube is the relatively new single-photon silicon photomultiplier (SPM) detectors. These devices convert the light from the scintillator to electrical pulses without amplification electronics. One advantage of these devices is that they do not require high voltages. Semiconductor detectors of various types can also be used in the hodoscopes. Many of these detectors are available off-the-shelf. As explained in the Background section, high-purity germanium detectors provide much better resolution than the NaI detectors, but are much more expensive and require cooling (typically with liquid nitrogen).

Other Variations

The embedded-hodoscope detector array positioned inside the reactor concrete shield wall immediately adjacent to 14 might be inserted at any distance along the axis of the collimating channel 8 in the biological shield 10 up to and as far as the plant containment building. The diameter of the hole drilled 16 is a parameter chosen according to design-basis objectives, such as desired spatial resolution and data collection time.

Each detector may be formed of a radiation-sensitive scintillation element to be stimulated by the gamma or neutron radiation and a photomultiplier tube to receive the output from the scintillator element. Several such elements may be placed in each detector assembly. Also, a lead radiation filter may be placed ahead of the detector in the collimator, and other lead filters may be placed in front of each subsequent scintillation element, respectively. Many gamma detectors are available which may be substituted for the sodium-iodide detector described in detail above.

The detection element can be a small sodium-iodide (thallium-activated) scintillation crystal, for example, or other gamma detector with energy discrimination capability. A photomultiplier tube or photodiode associated with each scintillator generates an electric signal that is proportional to the intensity of gamma radiation imposed on the scintillator. The signal from the photomultiplier or photodiode may be transmitted via conductor from the detector to the electronic analysis components and circuitry located outside of the biological shield. Also, with respect to preferred thermal-operation environment, the ambient temperature limit for scintillator detector and photomultiplier assemblies should be considered.

The invention would be well suited for application in large commercial liquid-cooled reactors, especially those yet to be placed in operation.

Therefore the scope of the present invention should be determined by the appended claims and not by the examples that have been given.

What is claimed is:

1. A radiation-monitoring diagnostic hodoscope system for producing an approximate image of radiation-producing components within and below a pressure vessel of shutdown nuclear plant, said system comprising:
   A) at least one gamma-radiation-monitoring hodoscope unit adapted to detect gamma radiation in a limited substantially-straight narrow radiation beam of less than 50 degrees and in at least one specific gamma-energy range, said at least one hodoscope unit comprising:
      1) a collimating means adapted to produce said narrow radiation beam and
      2) at least one radiation detector adapted to produce electrical signals corresponding to intensities of gamma radiation in said at least one specific gamma energy range;
   B) a positioning means for positioning said at least one hodoscope unit so as to accumulate sufficient radiation data representing radiation intensity and gamma energies in a sufficiently large number of narrow radiation beams to create said approximate image of said gamma radiation-producing sources within and below said pressure vessel; and
   C) a computer processor programmed with an algorithm adapted to associate said gamma or neutron radiation data so as to produce said approximate image of said radiation-producing components.

2. The system as in claim 1 wherein the at least one specific gamma energy range is at least two specific gamma energy ranges.

3. The system as in claim 1 wherein the processor is programmed to produce an approximate one-dimensional image.

4. The system as in claim 1 wherein the processor is programmed to produce an approximate two-dimensional image.

5. The system as in claim 1 wherein the processor is programmed to produce an approximate three-dimensional reconstructed image.

6. The system as in claim 1 wherein said system also comprises at least one neutron-radiation monitoring hodoscope.

7. The system as in claim 1 wherein said systems comprises at least one neutron- and gamma-radiation-monitoring hodoscope.

8. The system as in claim 1 wherein the nuclear plant is a boiling-water nuclear plant.

9. The system as in claim 1 wherein the nuclear plant is a pressurized-water-cooled nuclear plant.

10. The system as in claim 1 wherein the nuclear plant is a single nuclear plant of a group of nuclear plants consisting of: gas-cooled nuclear plants, liquid-metal-cooled nuclear plants, and heavy-water-cooled nuclear plants.

11. The system as in claim 1 wherein the at least one radiation detector is at least one scintillator detector.

12. The system as in claim 11 wherein the at least one scintillator detector is a sodium-iodide detector comprising a NaI scintillator.

13. The system as in claim 11 wherein each of the at least one scintillator detector includes a photomultiplier tube and a preamplifier.

14. The system as in claim 11 wherein each of the at least one scintillator detector includes a single photomultiplier for detecting light photons.

15. The system as in claim 1 wherein the at least one radiation detector is a bismuth-germanate-oxide (BGO) detector.

16. The system as in claim 1 wherein the at least one radiation-monitoring hodoscope unit is a plurality of such hodoscope units mounted external to the pressure vessel and adapted to function as plant-operation-monitoring instruments, as well as a real-time monitoring function of a shutdown nuclear plant, as well as monitoring such a plant while undergoing damaging or potentially damaging transients.

17. The system as in claim 16, wherein the damaging or potentially damaging transient includes one of a group of transients consisting of an accidental or uncontrolled loss-of-coolant condition, including melting of the reactor fuel, and melt-through of nuclear fuel through the bottom of the pressure vessel.

18. The system as in claim 16 wherein a biological shield surrounds the pressure vessel and at least a portion of the plurality of hodoscope units are mounted in or within the biological shield and pointed toward the pressure vessel so as to monitor gamma radiation produced within the pressure vessel.

19. The system as in claim 18 wherein the at least one hodoscope unit mounted within the biological shield is pointed to a region below the pressure vessel so as to monitor radiation originating in the region below the pressure vessel.

20. The system as in claim 18 wherein the at least one hodoscope unit is pointed to the region below the pressure vessel.

21. The system as in claim 16 wherein data obtained from at least some of the hodoscopes units is stored for later analysis.

* * * * *